(12) United States Patent
Balogh et al.

(10) Patent No.: US 7,695,974 B2
(45) Date of Patent: Apr. 13, 2010

(54) METHOD FOR IMAGING THE IONOMER SPATIAL DISTRIBUTION IN FUEL CELL ELECTRODES

(75) Inventors: Michael P. Balogh, Novi, MI (US); Frederick A. Hayes, Dixon, CA (US)

(73) Assignee: GM Global Technology Operations, Inc., Detroit, MI (US)

( * ) Notice: Subject to any disclaimer, the term of this patent is extended or adjusted under 35 U.S.C. 154(b) by 41 days.

(21) Appl. No.: 12/021,675

(22) Filed: Jan. 29, 2008

(65) Prior Publication Data

US 2009/0189076 A1   Jul. 30, 2009

(51) Int. Cl.
*G01N 21/75* (2006.01)

(52) U.S. Cl. .................. 436/167; 427/162; 427/497; 436/164; 436/166

(58) Field of Classification Search ............. None
See application file for complete search history.

(56) References Cited

U.S. PATENT DOCUMENTS 4,492,752 A * 1/1985 Hoffman et al. .......... 435/7.21
2006/0275227 A1* 12/2006 Subramanian et al. ........ 424/59

OTHER PUBLICATIONS

Swier et al, "Morphology control of sulfonated poly(ether ketone ketone) poly(ether imide) blends and their use in proton-exchange membranes". 2006. Journal of Membrane Science. vol. 270, pp. 22-31.*

* cited by examiner

*Primary Examiner*—Yelena G. Gakh
*Assistant Examiner*—David Weisz
(74) *Attorney, Agent, or Firm*—John A. Miller; Miller IP Group, PLC

(57) ABSTRACT

A method for evaluating the spatial distribution of an ionomer in a fuel cell MEA. The method includes embedding the MEA in an epoxy, and then slicing thin sections from the MEA. The sliced sections are then exposed to a titanium tetrachloride vapor that stains the epoxy. The stained sections are then viewed with, for example, a transmission electron microscope (TEM) where the lighter regions in the TEM image show the ionomer distribution.

16 Claims, 2 Drawing Sheets

METHOD FOR IMAGING THE IONOMER SPATIAL DISTRIBUTION IN FUEL CELL ELECTRODES

BACKGROUND OF THE INVENTION

1. Field of the Invention

This invention relates generally to a method for evaluating the ionomer spatial distribution in a fuel cell electrode and, more particularly, to a method for evaluating the ionomer spatial distribution in a fuel cell MEA including embedding the MEA in an epoxy, slicing sections of the MEA and then exposing the sliced sections to titanium tetrachloride vapors so as to stain non-ionomer materials in the MEA.

2. Discussion of the Related Art

Hydrogen is a very attractive fuel because it is clean and can be used to efficiently produce electricity in a fuel cell. A hydrogen fuel cell is an electro-chemical device that includes an anode and a cathode with an electrolyte therebetween. The anode receives hydrogen gas and the cathode receives oxygen or air. The hydrogen gas is dissociated in the anode to generate free hydrogen protons and electrons. The hydrogen protons pass through the electrolyte to the cathode. The hydrogen protons react with the oxygen and the electrons in the cathode to generate water. The electrons from the anode cannot pass through the electrolyte, and thus are directed through a load to perform work before being sent to the cathode.

Proton exchange membrane fuel cells (PEMFC) are a popular fuel cell for vehicles. The PEMFC generally includes a solid polymer electrolyte proton conducting membrane, such as a perfluorosulfonic acid membrane. The anode and cathode typically include finely divided catalytic particles, usually platinum (Pt), supported on carbon particles and mixed with an ionomer. The catalytic mixture is deposited on opposing sides of the membrane. The combination of the anode catalytic mixture, the cathode catalytic mixture and the membrane define a membrane electrode assembly (MEA). MEAs are relatively expensive to manufacture and require certain conditions for effective operation.

Several fuel cells are typically combined in a fuel cell stack to generate the desired power. For example, a typical fuel cell stack for a vehicle may have two hundred or more stacked fuel cells. The fuel cell stack receives a cathode input gas, typically a flow of air forced through the stack by a compressor. Not all of the oxygen is consumed by the stack and some of the air is output as a cathode exhaust gas that may include water as a stack by-product. The fuel cell stack also receives an anode hydrogen input gas that flows into the anode side of the stack.

The fuel cell stack includes a series of bipolar plates positioned between the several MEAs in the stack, where the bipolar plates and the MEAs are positioned between two end plates. The bipolar plates include an anode side and a cathode side for adjacent fuel cells in the stack. Anode gas flow channels are provided on the anode side of the bipolar plates that allow the anode reactant gas to flow to the respective MEA. Cathode gas flow channels are provided on the cathode side of the bipolar plates that allow the cathode reactant gas to flow to the respective MEA. One end plate includes anode gas flow channels, and the other end plate includes cathode gas flow channels. The bipolar plates and end plates are made of a conductive material, such as stainless steel or a conductive composite. The end plates conduct the electricity generated by the fuel cells out of the stack. The bipolar plates also include flow channels through which a cooling fluid flows.

It is known in the MEA art to coat the catalyst layer on the polymer electrolyte membrane. The catalyst layer may be deposited directly on the membrane, or indirectly applied to the membrane by first coating the catalyst on a decal substrate. Typically the catalyst is coated on the decal substrate as a slurry by a rolling process. The catalyst is then transferred to the membrane by a hot-pressing step. This type of MEA fabrication process is sometimes referred to as a catalyst coated membrane (CCM).

After the catalyst is coated on the decal substrate, an ionomer layer is typically sprayed over the catalyst layer before it is transferred to the membrane. Because both the catalyst and the membrane include the ionomer, the ionomer spray layer provides a better contact between the catalyst and the membrane, because it decreases the contact resistance between the catalyst and the membrane. This increases the proton exchange between the membrane and the catalyst, and thus, increases fuel cell performance.

The decal substrate can be a porous expanded polytetrafluoroethylene (ePTFE) decal substrate. However, the ePTFE substrate is expensive and not reusable. Particularly, when the catalyst is transferred to the membrane on the ePTFE substrate, a certain portion of the catalyst or catalyst components remain on the ePTFE substrate. Additionally, the ePTFE substrate stretches, deforms and absorbs solvents making a cleaning step very difficult. Hence, every ePTFE substrate used to make each anode and cathode is discarded.

The decal substrate can also be a non-porous ethylene tetrafluoroethylene (ETFE) decal substrate. The ETFE decal substrate provides minimal loss of catalyst and ionomer to the substrate because virtually all of the coating is decal transferred. The substrate does not deform and can be reused. For both of these processes, the anode and cathode decal substrates are cut to the dimensions of the final electrode size, then hot-pressed to the perfluorinated membrane, and subsequently, the decal substrate is pealed off.

As discussed above, the MEA includes a mixture of platinum supported on carbon particles that is mixed with an ionomer. The ionomer has a tendency to encapsulate the carbon particles, sometimes covering the platinum particles. In order to optimize the performance of the MEA, it is necessary to optimize the mixture that makes up the MEA. Thus, it may be necessary to differentiate the various materials in the MEA, such as the size of the carbon particles, the distribution of the platinum particles, the amount of the ionomer, the size and shape of the pores between the various materials, etc. One particular desire is to identify the spatial distribution of the ionomer in the fuel cell electrodes for MEA optimization purposes. Further, it is desirable to minimize the amount of platinum in the MEA because of its expense. However, because the different materials include some of the same components, such as carbon, it is difficult to differentiate them when looking through a microscope.

SUMMARY OF THE INVENTION

In accordance with the teachings of the present invention, a method is disclosed for evaluating the spatial distribution of an ionomer in a fuel cell MEA. The method includes embedding the MEA in an epoxy, and then slicing thin sections from the MEA. The sliced sections are then exposed to a titanium tetrachloride vapor that stains the epoxy. The stained sections are then viewed with, for example, a transmission electron microscope (TEM) where the lighter regions in the TEM image show the ionomer distribution.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a method for treating an MEA so that the spatial distribution of an ionomer in the MEA can be visually identified is merely exemplary in nature, and is in no way intended to limit the invention or its applications or uses.

Figure 1:
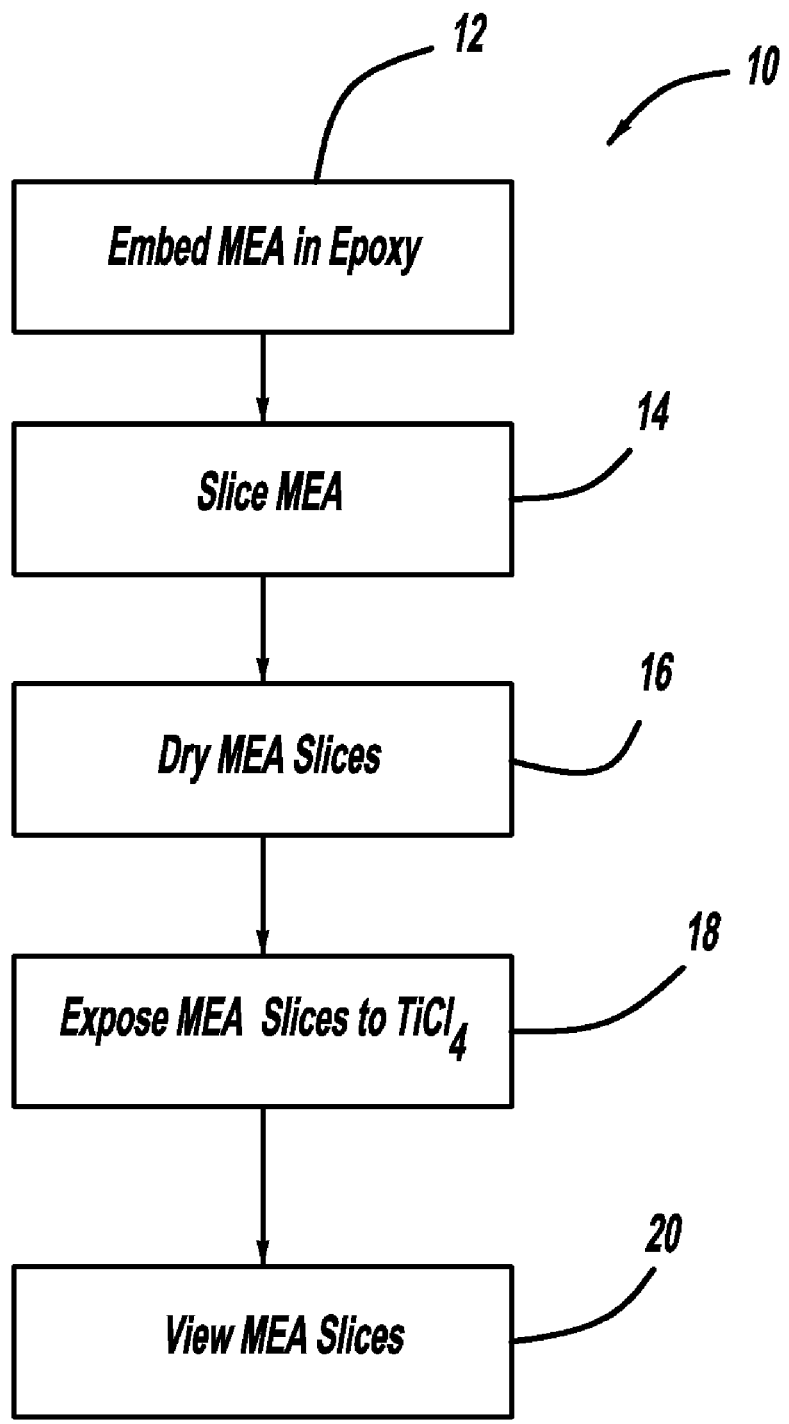
FIG. 1 is a flow chart diagram showing a process for treating an MEA so that the spatial distribution of the ionomer in the MEA can be evaluated, according to an embodiment of the present invention.

FIG. 1 is a flow chart diagram 10 showing a method for treating an MEA for a fuel cell so that the spatial distribution of an ionomer in the MEA can be visualized, according to an embodiment of the present invention. The process includes embedding the MEA in an epoxy at box 12. The MEA includes various shapes and sizes of pores between the carbon particles on which the catalyst is supported. Therefore, it is desirable to fill the pores with a clear substance, such as epoxy, so that the three-dimensional structure of the MEA can be viewed without the pores collapsing. Any suitable process for embedding the MEA in epoxy can be used. In one embodiment, the MEA is placed in a vacuum container, the gas is pumped out of the container, and the epoxy is dripped onto the MEA. When the pressure is reintroduced into the container, the epoxy is forced into the pores of the MEA.

The epoxy embedded MEA is then sliced or sectioned by, for example, a microtome machine, known to those skilled in the art, at box 14. The microtome machine slices very thin sections of the MEA at room temperature with a diamond knife. In this embodiment, the sliced sections of the MEA will be floating on the surface of the water in the microtome machine. The sliced MEA sections may be allowed to float on the water for some period of time, for example, five minutes, to absorb water. The sections are then collected from the water, and the MEA sections are blotted to remove excess water. The MEA sections are then allowed to dry for a certain period of time, such as 1-10 minutes, at box 16.

In one embodiment, the MEA sections are only partially dried. The partially dried MEA sections are then exposed to titanium tetrachloride ($TiCl_4$) vapor for a predetermined period of time, such as 1-2 minutes, at box 18. The titanium in the $TiCl_4$ only deposits on the embedded epoxy and the catalyst and carbon support, leaving the ionomer in the MEA sections unstained. Thus, the ionomer will be lighter than the epoxy, and is therefore easily visually differentiated from both the darker appearing epoxy and the darker appearing electrode catalyst. Any suitable imaging device can be used to view the stained MEA sections, such as a transmission electron microscope (TEM), at box 20. Thus, the MEAs sections can be characterized for controlling and optimizing the spatial distribution of the ionomer in the fuel cell electrodes.

Figure 2:
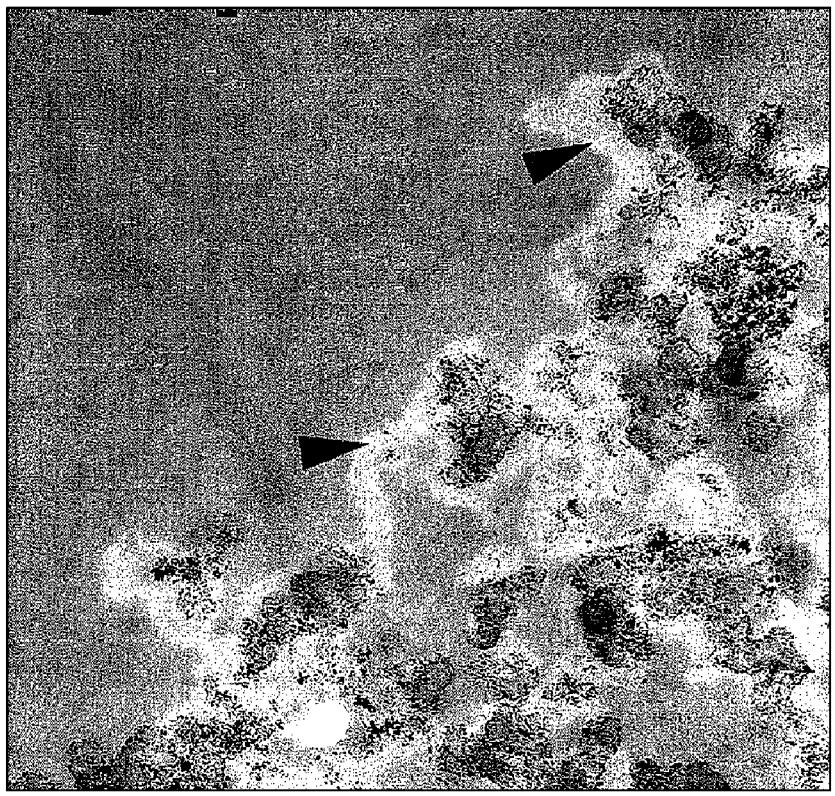
FIG. 2 is a magnified TEM micrograph of a cross-section of an MEA at a surface of the electrodes that has been treated by the process of the invention.
Figure 3:
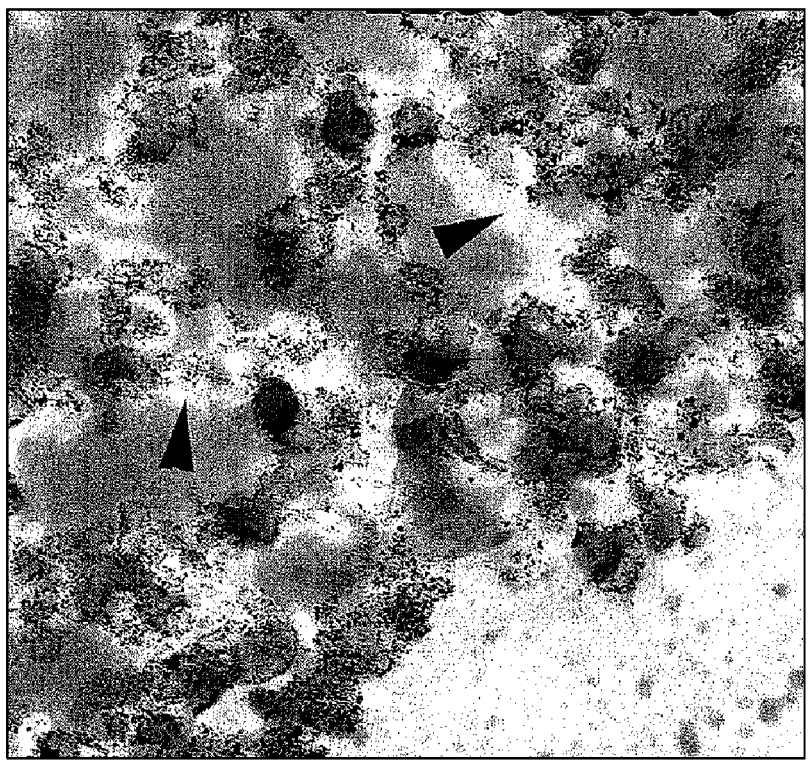
FIG. 3 is a magnified TEM micrograph of a cross-section of an MEA at an electrode/membrane interface that has been treated by the process of the invention.

FIGS. 2 and 3 are TEM micrographs of MEA sections at high magnification that have been stained by the process of the invention described above. In these micrographs, the ionomer appears as the lighter region, shown for example at the ends of the arrowheads, where the epoxy is the medium dark area and the carbon supported catalyst is the very dark regions. FIG. 2 shows a cross-section of the MEA near the surface of the electrode, where the consistent shaded region at the upper left is epoxy and the remaining portion of the micrograph is the electrode. FIG. 3 shows a cross-section of the MEA at the electrode/membrane interface, where the lighter region at the lower right of the micrograph is the membrane and the remaining portion of the micrograph is the electrode.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A method for evaluating the spatial distribution of an ionomer in a membrane electrode assembly (MEA), wherein the MEA includes electrodes that have an ionomer, said method comprising:
   embedding the MEA in a support material;
   slicing thin sections of the MEA;
   exposing the MEA sections to a staining material, wherein the staining material is titanium tetrachloride, that stains the support material in the MEA, but does not stain the ionomer, including the electrode ionomer; and
   viewing the MEA sections to identify the non-stained ionomer regions in the MEA sections.

2. The method according to claim 1 wherein exposing the MEA sections to titanium chloride includes exposing the MEA sections to a titanium tetrachloride vapor for a predetermined period of time.

3. The method according to claim 2 wherein exposing the MEA sections to titanium chloride vapor includes exposing the MEA sections to the titanium tetrachloride vapor for a period of one to two minutes.

4. The method according to claim 1 wherein exposing the MEA sections to titanium tetrachloride includes staining the support material with titanium in the titanium tetrachloride and leaving the ionomer in the MEA unstained.

5. The method according to claim 1 wherein slicing thin sections of the MEA includes using a microtome machine to slice the MEA.

6. The method according to claim 5 further comprising allowing the MEA slices to float on water in the microtome machine for a predetermined period of time.

7. The method according to claim 1 wherein embedding the MEA in a support material includes embedding the MEA in an epoxy.

8. The method according to claim 7 wherein embedding the MEA in an epoxy includes dripping the epoxy on the MEA in a vacuum environment and then exposing the MEA to pressure so that the epoxy is forced into pores in the MEA.

9. The method according to claim 1 wherein viewing the MEA sections includes using a transmission electron microscope.

10. The method according to claim 1 further comprising partially drying the MEA slices before they are exposed to the staining material.

11. A method for evaluating the spatial distribution of an ionomer in a membrane electrode assembly (MEA), wherein the MEA includes electrodes that have an ionomer, said method comprising:
    embedding the MEA in a support material;
    slicing thin sections of the MEA;
    exposing the sliced MEA sections to a titanium tetrachloride vapor for a predetermined period of time so that the epoxy is stained with titanium in the titanium tetrachloride and the ionomer in the MEA is unstained, including the electrode ionomer; and viewing the MEA sections with a transmission electron microscope to identify the non-stained ionomer regions in the MEA sections.

12. The method according to claim 11 wherein exposing the MEA sections to titanium tetrachloride vapor includes exposing the MEA sections to the titanium tetrachloride vapor for a period of one to two minutes.

13. The method according to claim 11 wherein slicing thin sections of the MEA includes using a microtome machine to slice the MEA.

14. The method according to claim 13 further comprising allowing the MEA slices to float on water in the microtome machine for a predetermined period of time.

15. The method according to claim 14 further comprising partially dying the MEA slices before they are exposed to the titanium tetrachloride vapor.

16. A method for evaluating the spatial distribution of an ionomer in a membrane electrode assembly (MEA), wherein the MEA includes electrodes that have an ionomer, said method comprising:

exposing the MEA to a staining material, wherein the staining material is titanium tetrachloride, that stains all of the materials in the MEA except the ionomer, including the electrode ionomer; and viewing the MEA to identify the non-stained ionomer regions in the MEA.

* * * * *